(12) United States Patent
Kulkova

(10) Patent No.: US 11,382,754 B2
(45) Date of Patent: Jul. 12, 2022

(54) BONE IMPLANT

(71) Applicant: TRACERAY OY, Turku (FI)

(72) Inventor: Yulia Kulkova, Turku (FI)

(73) Assignee: TRACERAY OY, Turku (FI)

( * ) Notice: Subject to any disclaimer, the term of this patent is extended or adjusted under 35 U.S.C. 154(b) by 333 days.

(21) Appl. No.: 15/772,937

(22) PCT Filed: Nov. 4, 2016

(86) PCT No.: PCT/FI2016/050782
§ 371 (c)(1),
(2) Date: May 2, 2018

(87) PCT Pub. No.: WO2017/077196
PCT Pub. Date: May 11, 2017

(65) Prior Publication Data
US 2018/0318088 A1    Nov. 8, 2018

(30) Foreign Application Priority Data
Nov. 4, 2015    (FI) .................................... 20155804

(51) Int. Cl.
*A61F 2/28* (2006.01)
*A61L 27/44* (2006.01)
(Continued)

(52) U.S. Cl.
CPC .......... *A61F 2/2846* (2013.01); *A61L 27/443* (2013.01); *A61L 27/446* (2013.01);
(Continued)

(58) Field of Classification Search
CPC .. A61F 2002/30586; A61F 2002/30588; A61F 2002/30583; A61F 2002/307; A61F 2002/3096
See application file for complete search history.

(56) References Cited

U.S. PATENT DOCUMENTS

2007/0296099 A1* 12/2007 Larsen ............... A61K 51/1244
                                                    264/4.1
2008/0154373 A1*  6/2008 Protopsaltis ....... A61B 17/7013
                                                    623/17.12
(Continued)

FOREIGN PATENT DOCUMENTS

EP    0 082 621    6/1983
EP    2 540 481    1/2013
(Continued)

OTHER PUBLICATIONS

Search Report dated Mar. 3, 2016 issued in Finnish Application No. 20155804 (2 pages).
(Continued)

*Primary Examiner* — Megan Y Wolf
(74) *Attorney, Agent, or Firm* — Nixon & Vanderhye

(57) ABSTRACT

The present invention provides a technological platform for bone regeneration. More specifically, the invention provides an implant comprising a plurality of polymeric casings at least one of which encases a bone void filler and at least one reinforcement component. Also provided is a method of regenerating bone by implanting one or more implants according to the present invention to a bone repair site.

25 Claims, 10 Drawing Sheets

(51) Int. Cl.
*A61L 27/48* (2006.01)
*A61F 2/30* (2006.01)

(52) U.S. Cl.
CPC ....... *A61L 27/48* (2013.01); *A61F 2002/2835* (2013.01); *A61F 2002/30062* (2013.01); *A61F 2002/30082* (2013.01); *A61F 2002/30677* (2013.01); *A61F 2310/00011* (2013.01); *A61F 2310/00161* (2013.01); *A61F 2310/00179* (2013.01); *A61F 2310/00329* (2013.01); *A61L 2430/02* (2013.01)

(56) References Cited

U.S. PATENT DOCUMENTS

| | | |
|---|---|---|
| 2013/0274890 A1 | 10/2013 | McKay |
| 2014/0031795 A1 | 1/2014 | McKay |
| 2014/0277569 A1* | 9/2014 | Lange ...................... A61F 2/28 623/23.51 |
| 2014/0316526 A1* | 10/2014 | Grotz ..................... A61F 2/3859 623/20.17 |
| 2015/0039097 A1 | 2/2015 | Biris |

FOREIGN PATENT DOCUMENTS

| | | |
|---|---|---|
| EP | 2 668 967 | 12/2013 |
| WO | 02/074353 A1 | 9/2002 |
| WO | 2006/114483 | 11/2006 |
| WO | 2009/048314 | 4/2009 |

OTHER PUBLICATIONS

Opinion on Patentability dated Mar. 3, 2016 issued in Finnish Application No. 20155804 (5 pages).
International Search Report for PCT/FI 2016/050782, dated Feb. 20, 2017, 3 pages.
International Preliminary Report on Patentability for PCT/FI 2016/050782 dated Mar. 12, 2018, 10 pages.

\* cited by examiner

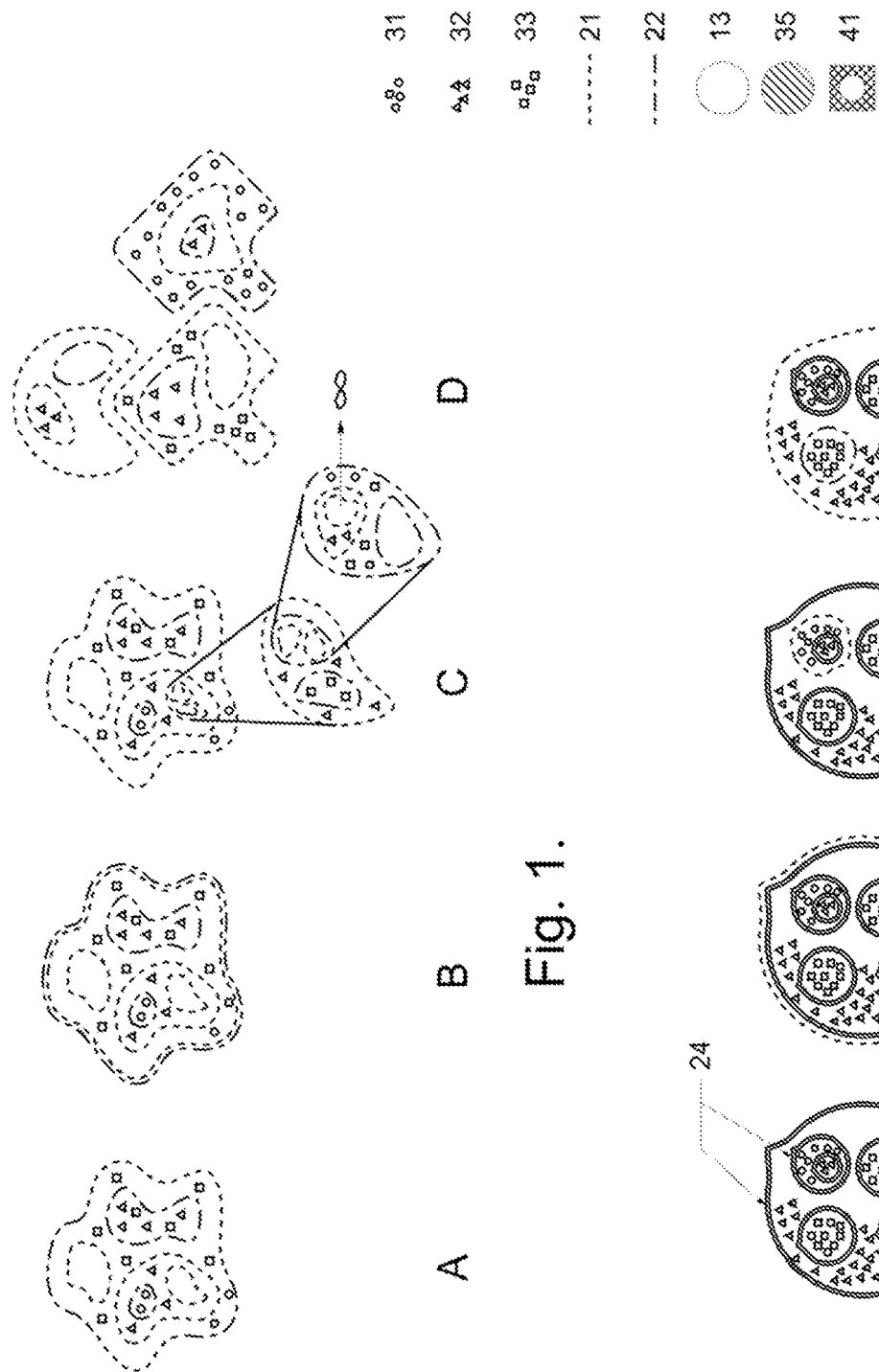

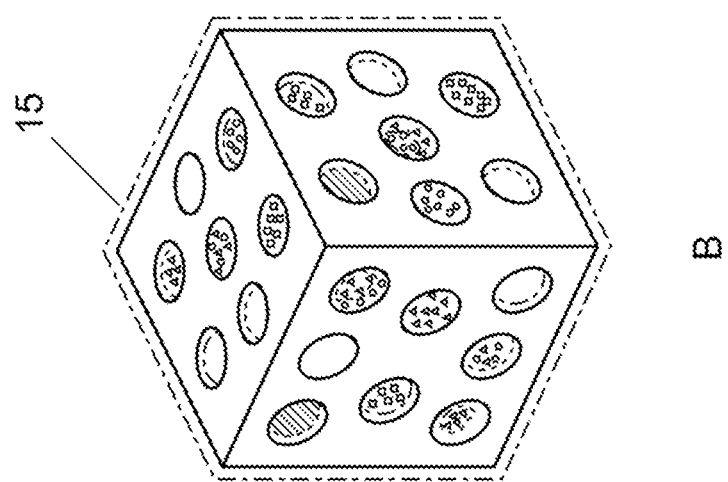
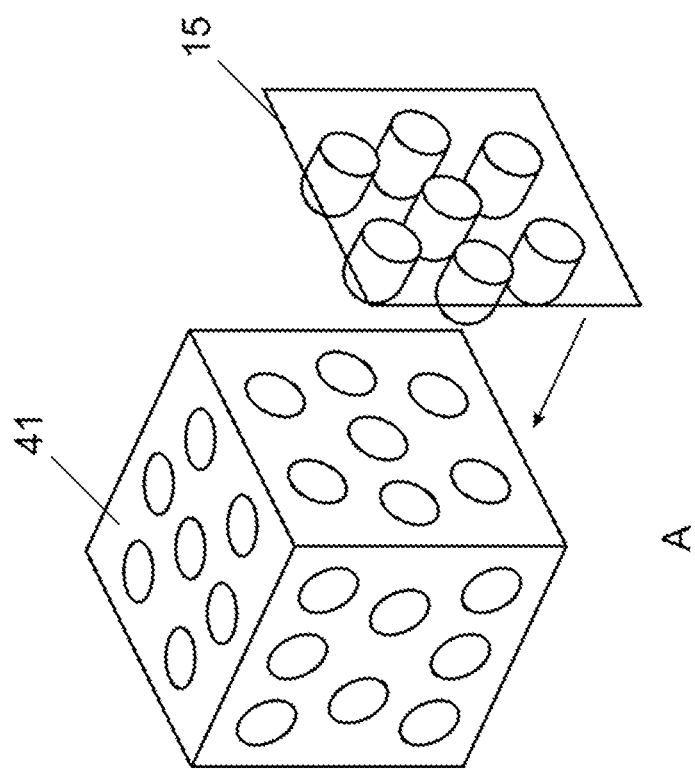
Fig. 4.

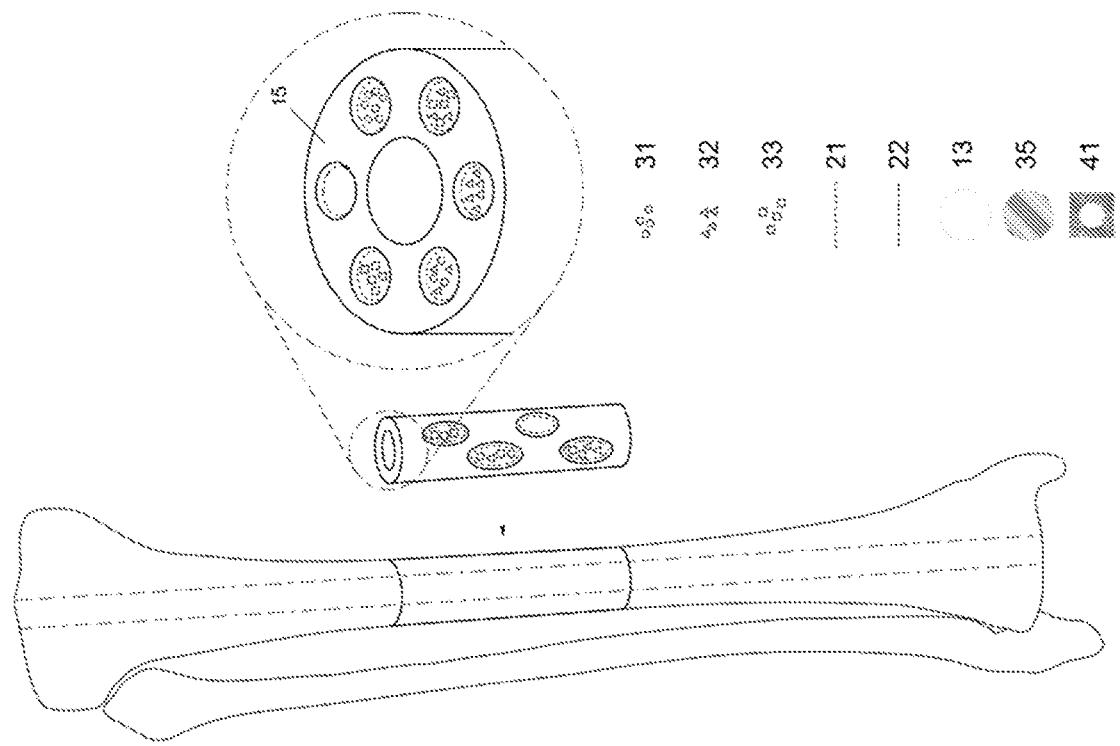
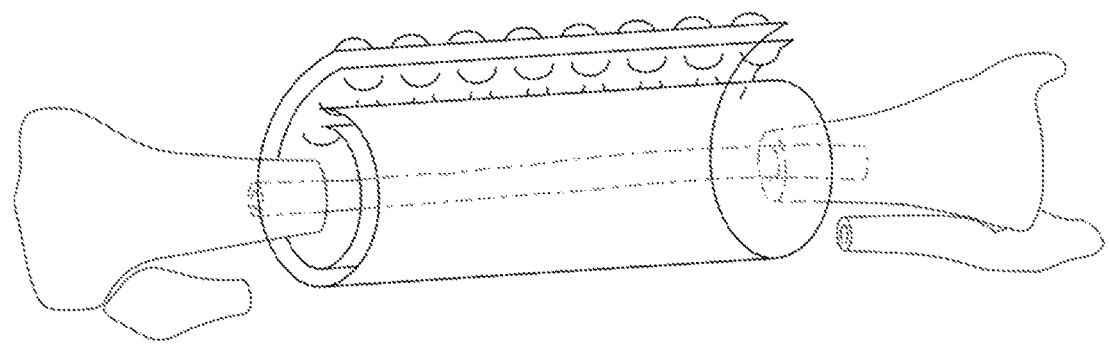
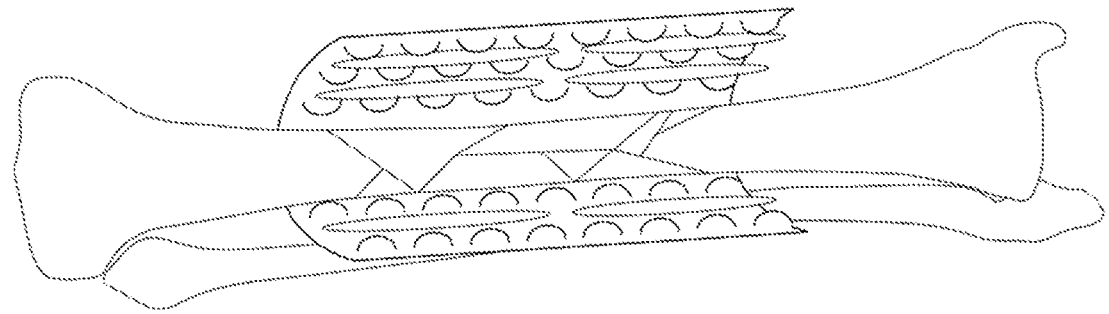
Fig. 6.

BONE IMPLANT

This application is the U.S. national phase of International Application No. PCT/FI2016/050782 filed 4 Nov. 2016, which designated the U.S. and claims priority to FI Patent Application No. 20155804 filed 4 Nov. 2015, the entire contents of each of which are hereby incorporated by reference.

FIELD OF THE INVENTION

This invention relates to a technological platform for use in bone regeneration. More specifically, the invention relates to a sophisticated bone implant and to a method of bone regeneration by implanting said implant to a bone repair site.

BACKGROUND OF THE INVENTION

Some specific cases of the present disclosure relate to veterinary orthopaedics. A vast amount of research into fracture management performed in veterinary practice in the past two decades, has led to the significant improvements in many treatment modalities. The understanding of the biology of the fracture site is a major breakthrough. The maintenance of the haematoma, the soft tissue attachments and adequate blood supply around the fracture side as well as the overall soft tissue enveloping are the key factors in the fracture healing process. In general, the accurate anatomic reduction allows preserving the normal biology of the fracture healing. However, in the case of comminuted fractures, extensive dissection is essential for the fragment reduction; hence, the mechanical stability gained by the reconstruction is relatively modest. Consequently, the rate of complications is high and includes infection, sequesters formation, delayed or non-union, and implant failure as a result of slow bone healing.

Metals are gold standard materials for veterinary orthopaedic implants. Metals are highly resistant to physiological loading conditions and corrosion in vivo; possess high strength, ductility and a good resistance to wear. However, despite the clinical success, metallic implants have intrinsic drawbacks. Physical forces and natural micromotions at the healing site profoundly control the biology of bone healing process. When the fracture healing process in long bones solely relies on the slow end-to-end union of the cortical bone, the use of traditional rigid metal plates might challenge the natural formation of the callus by diminishing the natural micromotions. The stiffness of the metals is much higher than that of bone. Therefore, when metallic implants introduced, the unfavorable load distribution, known as "stress-shielding" may occur. Stress-shielding, debris formation from multi-component implants and metallosis may result in peri-prosthetic bone loss and aseptic loosening of the implant. Due to the bone loss, the revision surgery could be significantly more complex with the increased risk of complications. In addition, the customized shape of the implant can only seldom be obtained.

Composites are promising alternatives to metallic implants. Composites are defined as materials which contain at least two distinct constituent materials or phases. Typically, composites contain a reinforcing phase and a matrix which binds the composite structure together. The characteristics of the composites are different compared to those of the individual components, e.g. plain polymers or ceramics. Bioresorbable composites typically contain a continuous polymer matrix phase and discontinuous osteoconductive ceramic phase, e.g. ceramic bioactive particulate made of e.g. calcium phosphate-based (Ca—P) ceramics, bioactive glass (BAG) etc.

Osteoconductive Ca—P ceramics have received considerable attention owing to their similarity to the bone mineral phase, hydroxycarbonate apatite, in terms of chemical composition and structure. In long term of implantation, Ca—P ceramics elicit extracellular response, providing a suitable surface for cellular attachment and are gradually replaced by bone. These biomaterials are commonly used as bone graft substitutes or as coatings on implants in medical applications. Implantable forms of Ca—P ceramics include particulates, blocks and injectable materials, e.g. bone cements. Osteoconductive Ca—P ceramics can be of natural origin, e.g. xenogenic bone mineral, or synthetic. Synthetic osteoconductive ceramics include hydroxyapatite (HA), tricalcium phosphates (TCP) and biphasic calcium phosphates (BCP) which consist of mixed HA and TCP phases in different ratios.

BAG was initially introduced by Larry Hench in the early 1970s. Typically, BAG is based on silica or phosphate and can be e.g. melt-derived or sol-gel derived. Bone-bonding, a distinctive feature of BAG is achieved via the formation of a bone-like hydroxyapatite (HA) layer on the material surface when in contact with aqueous solutions. In addition, BAG is effective in inhibiting the bacterial growth of more than 50 species. BAG (45S5, S53P4) has been approved by the US Food and Drug Administration and used as a bone graft substitute in more than a million patients. However, challenges are set by the design and fabrication of BAG containing products. Clinically, BAG is used mostly as particulate. This type of product possesses poor handling characteristics especially when there is a need for precise insertion or combination with an implant.

During the past decades, extensive research has been conducted in the field of biomaterials which introduced many innovations. For example, European patent application EP2668967 describes a composite implant combined with bioactive ceramics. The implant is comprised of at least two layers of fibre-reinforced composite and bioactive material arranged between said at least two layers. These types of implants are beneficial for several clinical applications, e.g. skull reconstructions; however, they lack flexibility and diversity which are crucial features in fracture management.

Thus, there is a need for advanced versatile bioactive implants with their shape and function being able to tackle particular clinical issues in skeletal reconstructions which can be achieved in situ.

BRIEF DESCRIPTION OF THE INVENTION

In one aspect, the present invention provides a bone implant comprising an array of a plurality of adjacent polymeric casings (10, 15) at least one of which encases a bone void filler (30), wherein said filler is not attached to its casing, and at least one reinforcement component (40).

In some embodiments, the reinforcement component (40) is encased by one of said plurality of casings, which casing is other than the one encasing the bone void filler (30). In such cases, the casing of the reinforcement component may be empty upon manufacture, and can be filled with the reinforcement component or an element thereof, such as the reinforcement phase, on clinical premises or in situ. The reinforcement component may comprise a reinforcement phase and a curable matrix substance.

In those embodiments, wherein the reinforcement component (40) is encased by one of said plurality of casings (10, 20), which casing is other than the one encasing the bone void filler (30), it is also possible that the reinforcement component is prefilled with pre-impregnated or non-pre-impregnated reinforcement phase upon manufacture, and to be filled further with a curable matrix substance, optionally with further pre-impregnated or non-pre-impregnated reinforcement phase, on clinical premises or in situ.

In the above embodiments, the reinforcement phase may comprise material selected from carbon, glass, ceramics, metals, synthetic or semi-synthetic polymers such as polyamides (including aramids such as Kevlar), polyimides, polyethylene or other aliphatic or aromatic hydrocarbons, acrylate polymers, and natural polymers including vegetable or animal fibres such as cellulose or spider silk, or other reinforcement materials known to those skilled in the art, and any mixtures or combinations thereof. Furthermore, the reinforcement phase may be provided in the form selected from the group consisting of randomly oriented fibres, intermingled fibres, overlaid fibres, juxtaposed fibres, woven or non-woven structures, fabrics or mats, or particulates, or whiskers, and 3D-printed fibre structures.

In some embodiments, the curable matrix substance may be selected from the group consisting of substituted, unsubstituted, or functionalized polycarbonates, polyethylene or other aliphatic or aromatic hydrocarbons, saturated or unsaturated polyesters, polyethers, polyurethanes, epoxy resins, acrylates, substances derived from nature such as collagen, chitosan or rubber, and other cross-linkable substances known to those skilled in the art. Non-limiting examples of suitable acrylates include those selected from the group consisting of dimethacrylates, methacrylates, methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA), and any mixtures or combinations thereof.

In some further embodiments, the casing of the reinforcement component (40) may comprise a removable projecting part (14) for collecting air when the casing is to be filled.

It is also possible that the reinforcement component (40) is not provided inside a casing. However, such a reinforcement component is in contact with the array of a plurality of casings. In such cases, the reinforcement component may comprise material selected from the group consisting of metals, reinforced or non-reinforced composites, self-reinforced polymers, ready composites, and bioresorbable materials. The reinforcement component may be provided in any form, such as a plate, and/or it may comprise at least one through hole.

In any of the above embodiments, at least one of the casings comprises at least one through hole (12), wherein the hole is not open to the interior of the casing. Preferably, said at least one through hole is comprised in the casing of the reinforcement component (40).

The reinforcement component (40) may form a backbone of the implant. The casings other than that of the reinforcement component (if any) are arranged in one or more arrayed wing-like structures (15) located on the same or different sides of the backbone.

In some embodiments, any one or more of the casings may encase a series of any number of adjacent and/or nested inner casings.

Casings of the present implant may, independently form each other, be made of a material selected from the group consisting of bioresorbable polymers, biostable polymers, BAG, composites of bioresorbable polymers, composites of biostable polymers, composites of bioresorbable polymers and BAG, and composites of bioresorbable polymers and Ca—P-based ceramics.

In some embodiments, the bone void filler (30) may be selected from the group consisting of calcium phosphate-based ceramics, bioactive glasses, bioactive glass-ceramics, composites of bioactive glasses or glass-ceramics and bioresorbable polymers, allograft or autograft bone, or fully or partly demineralized bone matrix.

In some embodiments, the bone void filler (30) may comprise any bioactive ceramic mentioned above containing radioactive isotopes, such as Holmium, for local radiotherapy of benign and malignant bone tumors.

In any of the above embodiments, at least one of the casings may encase a substance selected from the group consisting of buffering solutions (35), antibiotics, immunosuppressants, immunostimulators, anti-inflammatory agents, proteins, growth factors, cells, air, inert gasses, or any mixtures or combinations thereof.

The bone implant may have a stackable profile, and/or at least one of the casings and/or contents of at least one of the casings may be prepared by 3D printing, vacuum pressing, or any other forming technique.

In another aspect, the present invention provides a set of present implant, or an implant comprising multiple implant units, which units, independently from each other, may be as the implant defined above. In some embodiments, such units or members of the set of implants may have matching mating profiles.

In a further aspect, the present invention provides a method of treating a human or animal subject in need of bone grafting, bone fracture management, or local radiotherapy of benign and malignant bone tumors, said method comprising introducing the present implant or a set of implants the bone area to be treated.

Other aspects, embodiments, details, and advantages of the present invention will become apparent from the following figures and detailed description.

BRIEF DESCRIPTION OF THE DRAWINGS

In the following the invention will be described in greater detail by means of preferred embodiments with reference to the attached drawings, in which FIGS. 1A to 1D illustrate basic structures of some embodiments of the present implants.

In FIG. 1A, the implant is a nested structure of polymeric casings (21, 22) within other casings. In this embodiment, each internal casing is empty, fillable or filled e.g. with a filler (31, 32, 33), buffering solution (35), or further internal casings.

FIG. 1B demonstrates that an outer casing may be implemented in several layers.

FIG. 1C illustrates that a nested structure of casings within casings can continue until the physical limits are encountered.

FIG. 1D shows that an outer shape of casings can allow for stacking of the casings into two or three-dimensional clusters of casings.

FIGS. 2A to 2D illustrate basic structures of some embodiments of the present implants, wherein at least one of the casings is made of BAG (24).

FIG. 2A illustrates that casings may be prepared from BAG (24) e.g. by blowing or by three-dimensional printing.

FIG. 2B illustrates that an outer casing may be implemented in several layers of similar or dissimilar materials, e.g. BAG (24) and polymers (21, 22) or composites.

FIG. 2C illustrates that internal casings may be prepared of similar or dissimilar materials.

FIG. 2D illustrates that an outer casing may be made from polymers or composites, while at least some of the inner casings may be made of BAG (24).

FIG. 3A illustrates that casings may be arranged into a two-dimensional sheet-like array of adjacent casings connected with or attached to each other through a sealing area.

FIG. 3B illustrates that arrays of casings may contain different casing elements. These can be filled with a filler (31, 32, 33), e.g. BAG, contain a buffering solution (35), or be left empty (13), i.e. be fillable. The degradation rate of the casing elements may be adjusted to be faster for some of the elements and slower for the other elements, e.g. to release a buffering solution before the BAG-containing casing is degraded.

FIG. 3C illustrates that casings may also be arranged into a three-dimensional array of casings.

FIG. 3D illustrates that the shape of arrays of casings may allow for stacking of the arrays of casings into two or three-dimensional clusters.

FIGS. 4A and 4B show schematic illustrations of non-specific bulk implants according to some embodiments of the present invention. It is noteworthy that the shape of the bulk implant may vary endlessly, and the cubic shape shown is purely for illustrative purposes.

FIG. 4A illustrates a resilient array of casings (15) incorporated into a bulk of an implant (41).

FIG. 4B illustrates that a resilient array of casings (15) may encase a bulk implant. The array of casings casing may be implemented in several layers.

FIG. 5A illustrates that a series of present implants may be stacked to fill in the defect. Alternatively, a resilient array of casings (15) can be implanted so that the casings are stackable to each-other.

FIG. 5B illustrates that an implant made of a resilient array of casings (15) allows tight filling of the defect.

FIG. 5C illustrates an embodiment wherein a two-dimensional sheet-like resilient array of casings (15) is folded to fill in the defect.

FIG. 5D illustrates an embodiment wherein a bulk implant created e.g. from CT-scans by CAD-CAM and incorporated with a resilient array of casings (15) is used for filling the defect.

FIGS. 6A to 6C demonstrate the use of implants according to some embodiments of the present invention for the treatment of bone defects. The implants may be implemented in conjunction with other skeletal implants, e.g. plates and/or intramedullary nails known the art.

FIG. 6A shows the treatment of comminuted fractures by wrapping a sheet-like array of casings according to the present invention around the fracture segments. Bone chips may be attached in the wrap.

FIG. 6B shows the treatment of a segmental tibial defect by a fibular graft and a wrap (or several layers) of a sheet-like array of casings according to the present invention.

FIG. 6C shows the treatment of a segmental tibial defect with a tubular-shaped array of casings.

FIG. 8A shows an implant with a plurality of casings having the same dimensions.

FIG. 8B shows an implant with a plurality of casings having different dimensions.

FIG. 8C shows an implant comprising a plurality of casings with different dimensions, and some of the casings having through holes (12) extending from the top surface to the bottom surface. The holes are not in connection with the interior of the casing. In other words, the holes are surrounded by respective casing materials.

FIG. 8D shows that one or more casings may be stacked on top of a larger casing.

FIG. 8E shows a cross-sectional image illustrating different configurations of casings with different parts made of different materials (21, 22, 23), sealing areas (11), and holes (12). A casing with a hole can be empty, fillable, or filled with a substance.

FIGS. 9A to 9M illustrate different configurations of a bone implant comprising an array of a plurality of adjacent interconnected resilient casings that may be bioresporable or biostable.

FIGS. 9A to 9T show different configurations of implants with one or more reinforcement components (40) with holes or without holes, provided either inside one of the casing of an array of plurality of casings. Reinforcement components may also be provided as separate bone implants (41, dashed line), such as bone implants (e.g. plates) already known in the art. Such reinforcement component (41) is not provided inside any casing but it is in contact with the array of casings. The reinforcement component (41) may be with holes or without holes. The casings not comprising any reinforcement component are arranged in one or more wing-like structures or projections on the same or different sides of the reinforcement component, be it inside or outside a casing.

In FIGS. 10A and 10B, the units are repeated (dashed structure) in one dimension; while in FIG. 10C the units are repeated (dashed structure) in two dimensions. Stacking of the units may be used to extend the implant in a third dimension.

FIGS. 11A to 11D illustrate an embodiment of an arrayed implant structure, wherein a fillable casing comprising through holes forms the backbone of the implant. The other arrayed casings are configured as two wing-like structures on opposing sides of the backbone as in FIG. 9B or a single wing-like structure on one side of the implant as in FIG. 9A. Such an implant is particularly suitable for the treatment of bone fractures in small animals.

FIG. 11A demonstrates that the implant may be fixed e.g. by means of screws inserted into the holes in one of the casings.

FIG. 11B demonstrates that an empty casing may be filled by a curable matrix substance with or without reinforcement (43) in situ. Thereafter, the matrix substance solidifies to create a load-bearing backbone of the implant.

FIG. 11D is a cross-sectional image of a bone implant comprising casings with different parts made of different polymers (21, 22, 23), sealing areas (11), and holes (12). The casing with the holes (12) is filled with a reinforcement component (4), while the other casings are filled with different bone void fillers (31, 32).

DETAILED DESCRIPTION OF THE INVENTION

Figure 3:
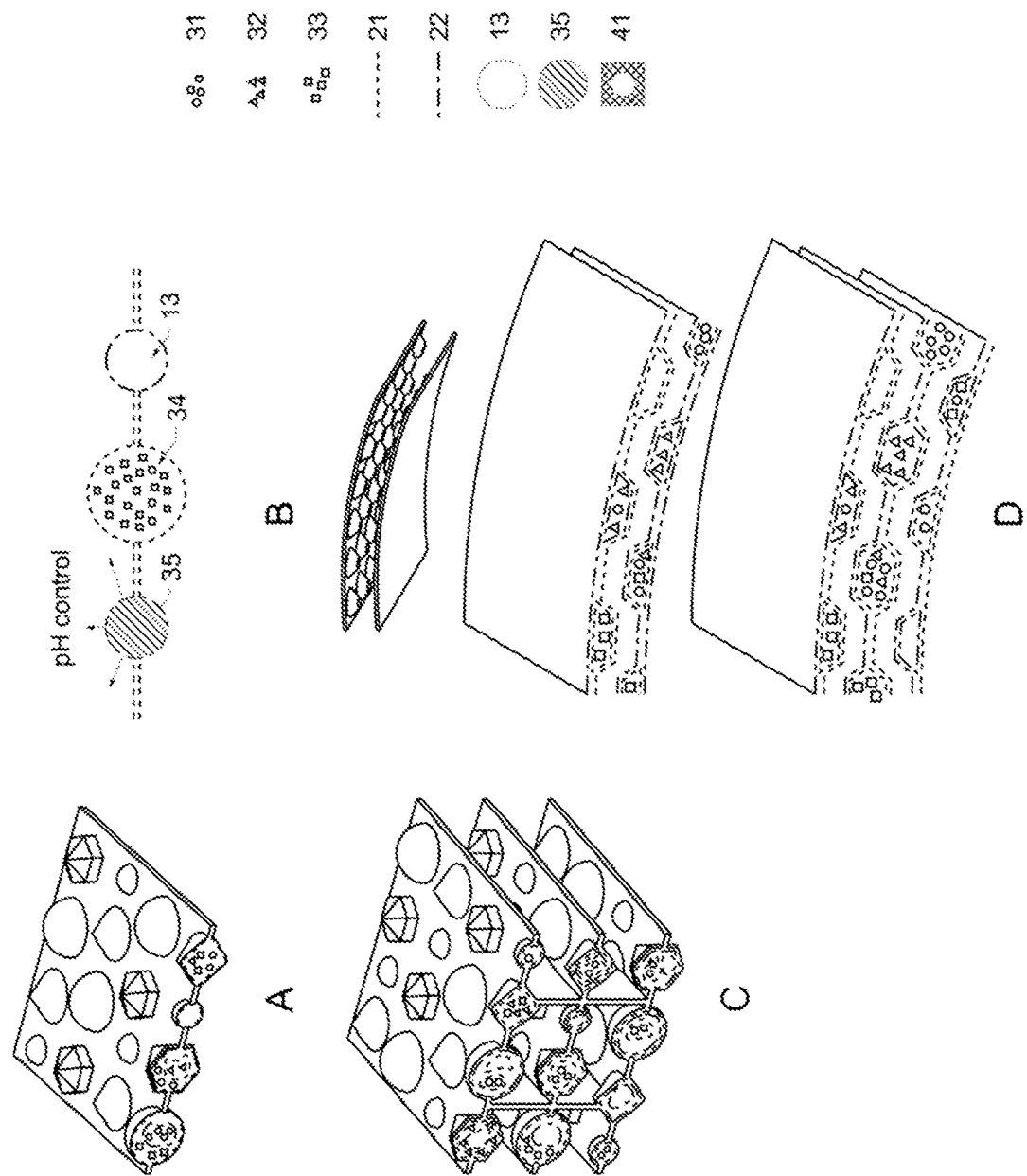
FIGS. 3A to 3D illustrate some embodiments with one or more arrays of casings.

This invention relates to a technological platform for use in bone regeneration. More specifically, the invention relates to an implant comprising an array of adjacent polymeric casings at least one of which contains a bioactive bone void filler material, wherein said filler is not attached to its casing, and at least one reinforcement component (40). The reinforcement component (40) is not in contact with the bone void filler.

As used herein, the term "or" has the meaning of both "and" and "or" (i.e. "and/or"). Furthermore, the meaning of a singular noun includes that of a plural noun and thus a singular term, unless otherwise specified, may also carry the meaning of its plural form. In other words, the term "a" or "an" may mean one or more.

As used herein, the term "bone grafting" refers to a surgical procedure that is used to place an implant of autogenious/allogenious/xenogenious bone or bone graft substitutes or bone void fillers into spaces around a broken bone or in a bone defect. The implant may be secured in place with mechanical means such as pins, plates, screws, or other fixtures, and/or with chemical means such as glues or adhesives.

The purpose of bone grafting may be any type of bone repair such as healing of fractures, especially multiple or complex fractures or those that do not heal well after an initial treatment, repair of bone defects, i.e. regeneration of bone lost to disease, infection, or injury, as well as healing of bone tissue around surgically implanted devices, like joint replacements, plates, or screws. Such bone grafting may be applied to any area or part of the body, and include, for instance, orthopaedic, dental, and veterinary purposes.

Subjects for bone grafting may be humans or animals. Thus, the present disclosure can be applied for both human and veterinary clinical applications. Accordingly, the term "subject" includes, but is not limited to, mammals such as humans, as well as domestic animals such as livestock, pets, race horses and other sporting animals. Examples of such animals include without limitation carnivores such as cats and dogs; swine, including pigs, hogs, and wild boars; ruminants and/or ungulates such as cattle, oxen, sheep, giraffes, deer, goats, bison, and camels; and horses.

As used herein, the term "casing" refers to an implant's closed or closable structural component that encases or surrounds its contents. The term "casing" is interchangeable with the terms "shell", "capsule", "enclosure", "package", "containment", and the like. Expressions like "a casing comprising" or "a casing containing" refer to the casing structure or material per se, not to any possible contents comprised or contained therein.

In some further embodiments, an implant may comprise nested casings, i.e. one or more casings within a casing. In such embodiments, the term "outer casing" refers to the outermost casing of a single implant. The outer casing defines the physical boundaries of an implant according to the present invention. Accordingly, the term "inner casing" or "internal casing" refers to any casing within another casing, be it an outer casing or another inner casing.

Each casing creates an interior that may be referred to by interchangeable terms such as "compartment", "cavity", "pocket", "space", "inner space", etc. Expressions like "contents of a casing" refer to any possible matter or substance comprised or contained in the casing, within the casing or inside the casing.

As used herein, the term "plurality of" refers to at least 2 or more, including, e.g., at least 3, at least 4, at least 5, at least 10 or more.

As used herein, the term "one or more" refers to one or any number greater than one, including e.g. at least 2, at least 3, at least 4, at least 5, at least 10 or more. The term "one or more" is interchangeable with the term "at least one".

Unless otherwise indicated, each of the plurality of casings may differ, independently from each other, in terms of their structural and functional features, such as composition, degree of biocompatibility, bioresorption rate, porosity (if any), size, shape, configuration, manner of interconnection with other casings, and contents. Consequently, also the compartments formed by each of the plurality of casings may differ, independently from each other, in terms of structural features, such as size and shape. Moreover, different compartments may have different contents and thus provide different functional effects, such as load-bearing capacity or bioactivity including, but not limited to, osteogenic, osteoinductive, osteoconductive and/or antibacterial properties.

As used herein, the term "biocompatible" refers to an agent, material or implant that, upon administration in vivo, is compatible with living tissues and does not induce substantial undesirable long-term effects, such as toxicity reactions or immune responses. Biocompatible agents, materials, or implants may, however, without compromising their biocompatibility, cause mild, transient inflammation which accompanies implantation of essentially all foreign objects into a living organism and which is also associated with the normal healing response. All components to be used in the present implants should be biocompatible.

As used herein, the term "bioresorbable" refers to a material that, when in contact with physiological fluids, starts to degrade but preserves its mechanical properties for a certain period of time, thereafter being safely absorbed and excreted by the body. In other words, bioresorbable materials disappear over time and do not require mechanical removal. The term "bioresorbable" may be used interchangeably with the terms "resorbable", "biodegradable", "bioerodable", and "bioabsorbable".

One or more of the plurality of casings comprised in the present implant may, independently form each other, be made of a material selected from the group consisting of bioresorbable polymers, biostable polymers, BAG, composites of bioresorbable polymers, composites of biostable polymers, composites of bioresorbable polymers and BAG, and composites of bioresorbable polymers and a Ca—P-based ceramic (e.g. HA, α-TCP, β-TCP, or BCP). Different casings in a single implant may be made of the same or different bioresorbable materials depending on the desired structural and/or functional properties of the casings.

In some embodiments, a casing comprised in the present implants may comprise or be made of any biocompatible and bioresorbable polymer. Bioresorbable polymers include, but are not limited to, natural polymers such as polysaccharides and proteins, and synthetic polymers such as aliphatic polyesters, polyethers, polyorthoesters, polyphosphoesters, polyphosphazenes, polyanhydrides, polyols, polyacetals, poly(ester amides), polyamides, poly(amino acids), poly (aspartic acid), poly(alkyl cyanoacrylates), polysiloxanes, some polyurethanes, some aliphatic polycarbonates, and copolymers thereof. Non-limiting examples of suitable aliphatic polyesters include polylactic acid (PLA), also known as polylactide, including different forms of PLA, such as poly-L-lactide (PLLA), poly-D-lactide (PDLA) and poly-DL-lactide (PDLLA); polycaprolactone (PCL); polydioxanone (PDS); polyglycolic acid (PGA) and polyglycolide (PG), optionally copolymerised with lactic acid to form poly(lactic-co-glycolic acid) (PLGA), with ecaprolactone to form poly(glycolide-co-caprolactone) (PGCL), or with trimethylene carbonate (TMC) to form poly(glycolide-co-trimethylene carbonate) (PGA-co-TMC); and block copolymers such as PEO-PPO-PAA, PEO-PPO-PEO, PLGA-PEO-PLGA, PEG-PLG, PLA-PLGA, PEG-PCL-PEG, PEG-PLA-PEG, PEG-PLGA-PEG, PLGA-PEG-PLGA. Non-limiting examples of polyhydroxyalkanoates, polyesters produced by microorganisms, include polyhydroxybutyrates, polyhydroxyvalerates, and copolymers thereof, more specifically poly(3-hydroxybutyrate) (PHB), poly(3-hydroxybutyrate-co-3-hydroxyvalerate) copolymer (PHBV), poly(4-hydroxybutyrate) (P4HB), poly(3-hydroxybutyrate-co-3-hydroxyhexanoate) copolymer (PHBHHx), and poly(3-hydroxyoctanoate) (PHO). Non-limiting examples of bioresorbable polysaccharides include gelatin, collagen, starch, hyaluronic acid, chitosan, and alginate. Bioresorbable polymers and methods for the production thereof are available in the art.

In some embodiments, preferred polymers include, but are not limited to, polyvinylchloride, polyethylene, polycarbonate, polyanhydrides, polysaccharides, polyamide and polyesters. Any combination of these materials may also be used.

In some embodiments, a casing comprised in the present implants may comprise or be made of any biocompatible and biostable polymer. Biostable polymers include, but are not limited to polyolefins, silicones, polyurethanes, polyethersulfone (PES), polyamides, biostable polyesters.

Non-limiting examples of suitable polyolefins include but are not limited to polyolefins polyethylene (PE) and polypropylene (PP). Non-limiting examples of suitable polyurethanes include, but are not limited to thermoplastic polycarbonate-urethane (PCU), segmented polyurethane (SPU), thermoplastic silicone-polycarbonate-urethane (TSPCU), thermoplastic polyether-urethane (TPU), thermoplastic silicone-polyether-urethane (TSPU). Non-limiting example of suitable polyamide includes, but is not limited to nylon. Non-limiting examples of suitable biostable polyesters include, but are not limited to polyethylene terephthalate (PET) and poly (1,4-butylene terephthalate) (PBT).

In some further embodiments, the outer surface of each casing can be coated by e.g. bioactive ceramic particles (e.g. HA, Ca—P, BAG), proteins (e.g. fibronectin, vitronectin), therapeutically active agents (e.g. growth factors, antibiotics) and/or cells. Also any combination of these materials may also be used for the coating.

Rapid degradation of casings comprising or being made of polymers such as PLA, PGA and their copolymers may lead to the release of acidic products. The resulting high local acidity may cause adverse tissue reactions, including incomplete osteogenic replacement during implant resorption, sterile inflammatory response, local osteolysis and chondrolysis. In some embodiments of this invention, the casings are made of these polymers. In order to decrease the risk of local complications, ceramic particles, such as HA and TCP may be added to the polymer matrix to neutralize the acidic environment. Without being limited to any theory, the addition of these bioactive ceramic particles is also expected to improve osteoconductivity. In some embodiments of this invention, the above mentioned problem of the high local acidy can be solved in a different way. Namely, some of the casings may encase a substance, liquid or solid, to counterbalance the rapid acidification of the peri-implant space. For example, some of the casings may contain a buffering solution, bioactive ceramic granules or both. In particular, BAG is a preferred material for the purpose. Indeed, when BAG comes in contact with physiological solutions, it starts to react and release ions which raise the pH of the peri-implant space. Naturally, BAG granules or powder may be applied to neutralise the acidic environment created by polymer degradation products. In some embodiments, the system can also be used to decrease the pH of the peri-implant space or maintain the pH at a certain predefined level.

On the other hand, when the primary purpose of the implant is to introduce BAG into the defect area, the system may be used to counterbalance the undesired effects of BAG on the surrounding tissues. It should be noted that unlike polymers, which degrade through the bulk, BAG is a surface-active material. Therefore, with the same total weight and chemical composition of the particulate, granules of smaller size are more reactive than granules of larger size. Small granules may be useful in some clinical applications, but they may drastically increase the pH of the peri-implant space causing adverse tissue reactions. Hence, a buffering solution encapsulated in a casing in proximity to the particulate, e.g. two adjacent casings, a nested casing or a similar configuration, may provide means to soften the negative effects of BAG dissolution products on the host tissues.

Stiffness of a casing may vary from an embodiment to another embodiment. Also different casings in a single implant may differ in their stiffness. For instance, in some embodiments it may be advantageous to use soft or resilient casings, while in some other embodiments, hard or non-resilient casings may be more appropriate. For instance, resilient casings may enhance the flexibility and manipulability of the implant, while hard casings may possess greater load-bearing properties. In some embodiments, a single implant may contain casings of different stiffnesses. A person skilled in the art can readily choose an appropriate casing material depending on the desired softness or hardness of the implant. In some preferred embodiments, all casings in an implant are resilient but load-bearing properties are provided by at least one reinforcement component (40) located inside or loaded into a resilient casing. Alternatively, load-bearing capacity may be provided by a reinforcement component (40) separate from, but in contact with, the plurality of resilient casings, as is discussed in more detail below.

A person skilled in the art is also able to select a suitable casing material to be used in the implant, depending on the desired bioresorption rate of the casing in question. In some embodiments, biostable casing material can be used. Typically, the bioresorption rate may vary from instant or immediate resorption to resorption within several years. However, in different embodiments, other time frames are envisaged, too. Furthermore, different materials or material mixtures may be used in different casings of a single implant to provide casings with different bioresorption properties. Once resorbed, the casing releases its contents which will then act according to its functional properties.

In addition, areas of very fast resorption rate may be used to create pores into one or more casings in a single implant in situ. Porosity may also be created during the manufacturing process, for instance by producing a mesh casing. In both cases, the desired outcome may be achieved by using any available or future printing technology. Employing a sheet of a naturally porous casing material is another way of providing porosity. Each of the plurality of casings in a single implant may or may not, independently from each other, be porous depending on the desired functional properties thereof.

The casings may also have different sizes and shapes, i.e. they are not limited to any particular size or shape. In some embodiments, a single implant may contain multiple, such as two, three, or four, etc., differently sized and/or shaped casings and correspondingly formed compartments.

Any casing may be composed of at least two surfaces. Such a casing or an array of such casings may be constructed from two similar or dissimilar polymeric sheets (such bioresorbable or biostable sheets) that are attached to each other along their borders and/or other desired lines thereby forming one or more pockets or compartments. Such attached areas may be denoted as sealing areas (11). In an array of a plurality of adjacent casings, a first surface of said casings may be made of the same casing material, while some or all of the second surfaces may be made of different casings materials.

In some embodiments, at least one casing in a single implant may comprise one or more through holes (12) which extend from a first surface to a second surface. The holes (12) are surrounded by the casing material, which means that the holes (12) are not in contact with an interior of the casing through which they extend. In other words, the holes (12) are not open to the interior of the casing, and contents of the casing cannot escape through the holes (12). In some embodiments, at least one casing in an implant comprises one or more internal sealing areas, i.e. sealing areas that are not in contact with the sealing area that forms the borders of the casing, and the one or more holes (12) go through the one or more internal sealing areas. One internal sealing may comprise more than one through hole. Alternatively or in addition, one or more holes (12) may be arranged in the bordering sealing area. Fixing means such as bone screws may be inserted through the holes (12) and used for securing the implant in its place. Alternatively or in addition, the implant may be secured in its place by chemical means such as glue or an adhesive.

Contents of the plurality of casings, and compartments formed by said casings, in a single implant may vary depending on the purpose and details of the bone surgery. In addition to one or more bioactive bone void fillers, a casing may encase other bioactive agents, such as buffers, therapeutic agents, and cells as is disclosed in more detail below. An implant may also comprise one or more casings or compartments that are empty, or filled with air. Air-filled casings may be advantageous, for instance, for providing implants with concomitant stiffness and very light weight. In some embodiments, any inert gas or gas mixture may be used instead of air.

In some embodiments, one or more of the empty casings or compartments, if any, may be loaded with their contents only shortly before or during a bone surgery, i.e. on the clinical premises or in situ. Such casings or compartments may be called as fillable casings or compartments. For instance, in the case of closed fillable casings, the contents may be injected into the empty casing using a syringe and needle. Likewise, the air of an air-filled casing may be replaced with some other contents. For casings that are closable and fillable, the loading may be performed by any suitable manner, for instance, by moving the contents into its casing by using a spatula or syringe. Typical substances to be loaded on the clinical premises or in situ include substances whose activity might be compromised during storage and/or autogenic substances not available prior to the surgery, such as autogenic cells.

Alternatively or in addition, one or more reinforcement components (40) with load-bearing capacity, such as reinforcement phase and/or a curable matrix substance may be loaded into a fillable casing or compartment, be it closed or closable, on the clinical premises or in situ. The fillable casing may also be pre-filled with the reinforcement phase and/or the curable matrix substance to some extent upon manufacture, and further filled with the same or different reinforcement phase and/or curable matrix substance at the clinical premises or in situ. In these cases, an implant with one or more empty or prefilled casings or compartments may be placed inside or around a bone defect first, and then filled with said one or more components, optionally with further components such as bioactive agents, to provide tight fitting with the bone defect. In some further embodiments, said fillable casing comprises one or more holes (12) for screws or other fixation means, arranged in one or more internal sealing areas. The implant may be secured in its place prior to being filled with the reinforcement component (40). The casing of the reinforcement component may form the backbone of the implant, and have any desired size or shape. Non-limiting examples of preferred shapes include elongated shapes and any T-like shapes.

In accordance with the above, one or more of the plurality of casings may be loaded with their contents at, upon, or during manufacture, on the clinical premises or at the surgical site in situ. The latter two options are not limited to the loading of empty, air-filled, or closable casings but may also be applied to incorporating additional substances into one or more closed or closable casings already loaded with one or more substances during the manufacturing process.

In some embodiments, one or more of the plurality of casings in a single implant may be closable, i.e. open upon manufacture but closed after being filled on the clinical premises or in situ. Non-limiting examples of suitable closing mechanisms include bioresorbable strings, stitches, sutures, and any combinations thereof. A fillable casing may be either closed or closable, as well as either empty or prefilled as discussed in more detail elsewhere in the specification.

The present implant comprises at least one reinforcement component (40), which can be either inside or outside of a casing comprised in the implant. Each reinforcement component may be provided in a casing of its own, or more than one reinforcement component may be provided in one casing. Reinforcement components of a single implant may be provided inside or outside of casings in any desired proportions. Reinforcement components that are not provided inside any casing are, however, in contact with or connected to the present array of a plurality of casings. A reinforcement component not provided inside any casing may be connected to the array of casings upon manufacture, on the clinical premises, or in situ.

Non-limiting examples of reinforcement components (40) provided inside one or more casings of the plurality of casings, or outside any casing, include conventional plates, sheets or any other suitable structures made of or comprising metals, reinforced or non-reinforced composites (e.g. reinforced or non-reinforced polyether ketone, PEEK), self-reinforced polymers, ready composites, or bioresorbable materials. Reinforcement components may also comprise or consist of a reinforcement phase and a curable matrix substance. Typically, such a reinforcement component is provided inside a casing.

As used herein, the term "reinforcing phase" or "reinforcement phase" refers to material that provides load-bearing capacity or strength to the implant. Preferred examples of suitable reinforcement phases include, but are not limited to, those made of glass such as bioactive glass, S-glass, R-glass, D-glass, C-glass, E-glass, or A-glass, carbon, quartz, ceramic, metal, polyethylene, polyamide, polyimide, acrylate polymer, and any mixtures or combinations thereof. In some embodiments, a single implant may comprise one or more different types of reinforcement phases in any desired combination.

Reinforcement phase may be provided in dry form (i.e. as non-pre-impregnated) or as pre-impregnated with a curable matrix substance (i.e. as prepreg). Furthermore, the reinforcement phase may be provided, for example, in the form of short randomly oriented fibres or as longer fibres in the form of woven or braided structures, such as two-dimensional or three-dimensional fabrics or mats, non-woven structures, 3D-printed fiber structures, particulates or whiskers, or as intermingled, overlaid, or juxtaposed fibres. Such reinforcement phases gain their load-bearing capacity upon curing. Alternatively, the reinforcement phase may be a ready composite having its load-bearing properties present even without further need to be processed. In other words, the reinforcement phase may be provided in any desired form or as a combination of different forms.

Reinforcement phase may be loaded into a casing upon manufacture, on the clinical premises, or at the surgical site in situ. In some embodiments, a fillable casing with or without one or more holes (12) is loaded with a dry reinforcement phase upon manufacture and further filled with a curable matrix substance on clinical premises or in situ. In some other embodiments, a fillable casing with or without one or more holes (12) is loaded with prepreg upon manufacture, and further filled with a curable matrix substance on clinical premises or in situ. In some further embodiments, a fillable casing with or without one or more holes (12) is left empty upon manufacture but filled with a reinforcement phase (e.g. as prepreg) and a curable matrix substance on clinical premises or in situ. In some other embodiments, a fillable casing with or without one or more holes (12) is loaded with prepreg and a curable matrix substance upon manufacture. In some other embodiments, a fillable casing with or without one or more holes (12) is loaded with a dry reinforcement phase and a curable matrix substance upon manufacture. In some other embodiments, a fillable casing with or without one or more holes (12) is loaded with a reinforcement component that does not require further actions (e.g. metallic components, or components made of or comprising reinforced or non-reinforced composites (e.g. PEEK), self-reinforced polymers, ready composites, or bioresorbable materials). A reinforcement component that does not require further action may be loaded inside a casing upon manufacture, on the clinical premises, or in situ. If an implant comprises multiple similar or dissimilar reinforcement components, they may be loaded into their casings independently form each other upon manufacture, on the clinical premises, and/or in situ.

As used herein, the term "curable matrix substance" refers to a monomeric, oligomeric, or polymeric compound that can be cured, i.e. hardened, through polymerization or cross-linking using electromagnetic radiation or mechanical stimulation, or is self-curing, i.e. self-hardening by autopolymerization. Non-limiting examples of electromagnetic radiation include X-rays, microwaves, and light such as blue light or ultraviolet (UV) light. A non-limiting example of mechanical stimulation is ultrasound. Also chemical curing may be employed.

In some embodiments, an initiator or activator may be required for initiating the curing process as is well known in the art. Such an initiator may be provided as a component of the casing material, or loaded into a casing upon manufacture, on the clinical premises, or at the surgical site in situ.

Suitable curable matrix substances include substituted, unsubstituted, or functionalized polyesters, epoxies such as epoxy acrylate, and acrylates such as dimethacrylates and methacrylates including, but not limited to, methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA), and any mixtures or combinations thereof.

In some further embodiments, an empty casing or compartment to be filled on the clinical premises or at the surgical site in situ may comprise a projecting part (14), such as a projecting distal end, the purpose of which is to collect air when being filled e.g. with a reinforcement component, using a syringe or any other appropriate means. Once the casing is filled and cured, the protruding part may be detached or removed, for example by cutting.

At least one of the plurality of casings in a single implant comprises bioactive filler, also called bioactive bone void filler, which may be in contact with but is not attached to a casing surrounding said filler. As used herein, the term "bioactive" has a general meaning of having an effect on a living organism. To be more specific, "bioactive" may herein, depending on the embodiment, refer to one or more of osteogenic, osteoinductive, osteoconductive, and antibacterial properties or other therapeutic properties e.g. for local radiotherapy of benign and malignant bone tumors.

As used herein, the term "osteogenic" refers to the ability of an agent, material, or implant to enhance or accelerate the growth of new bone tissue by one or more mechanisms, such as osteogenesis, osteoinduction, osteoconduction, and/or osseointegration.

As used herein, the term "osteogenesis" refers to the development and formation of bone.

As used herein, the term "osteoinduction" refers to a process by which osteogenesis is induced, i.e. differentiation of new osteoblasts from undifferentiated pluripotent cells, namely osteoprogenitor cells, and subsequent formation of new bone. Accordingly, the term "osteoinductive" refers to the quality of being able to recruit immature cells from the host and to stimulate these cells form new bone.

As used herein, the term "osteoconduction" refers to apposition of bone directly on a surface on an implant generally without any intervening fibrous tissue. Accordingly, the term "osteoconductive" refers to the quality of being able to serve as a scaffold on which existing osteoblasts are able to grow.

As used herein, the terms "osteointegration" and "osseointegration" refer to a stable anchorage of an implant by direct bone-to-implant contact.

As used herein, the term "antibacterial property" refers to the ability of an agent, material, or implant to kill bacteria present in an area of implantation and/or to prevent growth of thereof. Such antibacterial properties are important in preventing surgical site infections.

Suitable bioactive materials for use as a bone void filler in the present implants include, but are not limited to, the following synthetic bone substitute materials: calcium phosphate-based ceramics, such as hydroxyapatite (HA), α-tricalcium phosphate (α-TCP), β-tricalcium phosphate (β-TCP), and biphasic calcium phosphates (BCP) which consist of mixed HA and TCP phases in different ratios; glass compositions, i.e. BAG; BAG-ceramics; related composite materials combining bioactive glasses or glass-ceramics with biodegradable polymers; and any mixtures or combinations thereof. Synthetic bone substitute materials and methods for the preparation thereof are available in the art. In some embodiments, a preferred bone void filler material is BAG.

In some embodiments, a bone void filler may be or contain a nonsynthetic bone graft material including, but not limited to, allograft or autograft bone in the form of chips, strips, granules, or the like, as well as fully or partly demineralized bone matrix (DBM) derived, for instance, from cortical, cancelleous and/or corticocancellous, preferably allogenic bone tissue. In some further embodiments, the bone void filler may be or contain a composite bone graft which comprises an allograft or autograft bone component, such as DBM, and a synthetic bone substitute, such as anyone or any mixture of the bone substitute materials disclosed above.

In some other embodiments, a bone void filler may be composed of synthetic bone substitute materials which contain radioactive isotopes, such as Holmium, for local radiotherapy of benign and malignant bone tumors.

As set forth above, at least one of the pluralities of casings in a single implant is loaded with a bioactive bone void filler. In other words, depending on the embodiment in question, any number of the plurality of casings in an implant may encase the same or different bone void filler.

Bioactive bone void fillers of the present implants may be used in different forms. For instance, the fillers may be used in the form of particulates, fine powder, porous shapes such as granules, fibers or chips, settable pastes, settable putties, suspension, or in any mixtures or combinations thereof.

Importantly, a bioactive bone void filler of the present implants may be in contact with but is not attached to its casing. In other words, each casing and its contents are separate physical entities, i.e. they are not different phases of a composite, although the casing itself may be made of a composite. Thus, the bone void filler is loose inside its casing.

The non-attached arrangement of a bone void filler and its casing serves at least two different purposes. Firstly, the shapaebility of the implant is better in embodiments in which the granules may freely move inside a soft casing. The second purpose applies to embodiments in which BAG granules are used as a bone void filler. As BAG is a surface reactive material, it is important that all granules have access to physiological fluids. If a composite was used as a bone void filler and if the matrix had low permeability to the physiological fluids, granules entrapped in a polymer matrix could be left unreacted, rendering the BAG granules useless.

A bioactive bone void filler may be packed in its casing at any suitable density. In some embodiments, the filler may be loosely packed in the casing so as to provide flexibility and manipulability. In other embodiments, the filler may be tightly packed in the casing so as to provide a relatively stiff implant with, for instance, enhanced load-bearing properties. In some further embodiments, the implant may contain both loosely and tightly packed casings in any desired ratios.

The present casings and implants may also comprise any additional bioactive agents such as osteogenic agents that enhance bone regeneration and/or medicaments that promote healing of the bone repair site, for timed release in situ. Such additional agents, or mixtures thereof, may be provided, independently form each other, as integral parts of one or more casing materials, inside one or more casings containing nothing else, and/or inside one or more casings which contain, for instance, the bioactive bone void filler. Any additional bioactive agents may be incorporated into said one or more casings upon manufacture, on the clinical premises, and/or at the surgical site in situ as is appropriate for the agent in question.

Preferred additional bioactive agents include, but are not limited to, medicaments such as antibiotics, immunosuppressants, immunostimulators, and anti-inflammatory agents, proteins such as osteocalcin, and osteoglycin, i.e. osteoinfuctive factor (OIF), and growth factors such as bone morphogenic proteins (BMP), e.g. BMP-2, -4, -6, -7 and -9, fibroblast growth factors (FGF), vascular endothelial growth factors (VEGF), platelet derived growth factors (PDGF), and transforming growth factors, such as TGF-β.

One or more of the plurality of casings may also encase cells for delivering them to the bone repair area. The cells may have been integrated with the casing, for instance, by culturing them on the casing material or by utilizing any available or future cell printing technique, or the cells may be encased in a suitable matrix, such as a hydrogel, under conditions which support survival of the cells, preferably on the clinical premises or at the surgical site. Non-limiting examples of cell types to be delivered include one or more of stem cells such as mesenchymal stem cells, bone marrow stromal cells, osteoprogenitor cells, osteoblasts, osteocytes, and osteoclasts. The cells may be either autogenic or allogenic.

One or more of the plurality of casings may also encase a buffering solution, either alone or together with at least one other substance such as a bone void filler or a population of cells. Typical non-limiting examples of suitable buffering solutions include normal saline, phosphate-buffered saline (PBS), lactated Ringer's solution, and acetated Ringer's solution.

The present implants may be constructed in different forms. For instance, in some embodiments the implant may be a nested implant meaning that a casing may lie within another casing. In some other embodiments, an outer casing may contain one or more adjacent inner casings. In some further embodiments, one or more of said adjacent inner casings may encase one or more further casings, and so forth. Thus, in some embodiments, the plurality of casings may comprise an outer casing which encases any number of adjacent or nested inner casings. As set forth above, these adjacent or nested casings may be similar, or they may differ in terms of material, size, shape, or thickness. Consequently, the nested casings may have similar or different functional properties.

FIGS. 1 and 2 illustrate non-limiting examples of nested structures of the present implants with varying levels of nested hierarchy. A single implant may comprise an outer casing and one or more (first level) inner casings, some, all, or none of which encase further (second level) inner casings, some, all, or none of which encase still further (third level) inner casings, and so forth. Each of the casings may be made of a bioresorbable polymer, biostable polymer, composite, or BAG, and a single implant may comprise casings made of the same or a different bioresorbable or biostable materials. Moreover, one or more of the casings in a single implant may also be implemented in two or more layers. At least one of the casings encases a bone void filler, or a mixture of bone void fillers, either alone or together with at least one other substance disclosed herein. The other casings may encase e.g. a reinforcement component, a buffering solution, a bioactive substance other than a bone void filler, cells, or any mixture thereof, or be left empty.

Not only may the plurality of casings in a single implant be interconnected adjacently or nestedly through their contents but said plurality of casings may also be interconnected through the bioresorbable or biostable casing material itself, for example in the form of a sealing area (11), e.g. by forming a contiguous array with a plurality of adjacent protrusion forming said casings. Such a structure resembles a bubble pack, a commonly used plastic wrapping material with regularly spaced, protruding air-filled hemispheres (bubbles). In the case of the present implants, however, shape of the casings is not limited to hemispheres but may vary without limitation. Moreover, the contents of the casings are not limited to air but may vary in accordance with different embodiments of the present invention. A single implant may contain casings with one or more different shapes and sizes. Furthermore, the array-like implant may or may not contain nested or adjacent inner casings.

FIGS. 3A to 3D, 6A, and 6B illustrate non-limiting examples of embodiments with one or more arrays of casings. The arrays may be two-dimensional sheet-like arrays of casings as in FIG. 3A, three-dimensional array of casings as in FIG. 3C, or stackable arrays of casings arrangeable into two or three-dimensional clusters as in FIG. 3D.

An advantage associated with the present array-like implant with a plurality of polymeric casings filled with bioactive substances is that, in some embodiments, the implant may be pliable and, thus, particularly suitable for being wrapped around a bone repair site, or for tightly fitting inside a bone defect, for instance. Once secured in its place by chemical or mechanical means disclosed in more detail above, one or more casings filled with a reinforcing component are hardened by curing, thus resulting in loss of pliability. Also, a pliable array-like implant may be easily cut to a desired size and shape during operation.

Not only can the implant be cut to a desired size and shape during the operation, but it may also be cut to contain only casings with a desired contents. Conveniently, sealing areas (11) of an implant may be used for such cutting. Thus, in some embodiments, the present implants are fully customizable. The customizability is further enhanced by the option of filling empty casings, or adding bioactive substances into pre-filled casings, on the clinical premises or at the surgical site in situ.

In some embodiments, the present bone implant comprises or consists of an array of a plurality of adjacent interconnected bioresorbable resilient casings, wherein at least one of the casings encases a bone void filler, wherein said filler is not attached to its casing, and at least one reinforcement component.

In some further embodiments of the above arrangement, at least one of the plurality of casings in an array-like (bubble pack) implant comprises bone void filler while at least one other casing is fillable with a reinforcing component.

In some further embodiments, the casing fillable with the reinforcing component is larger in size than the at least one casing comprising the bone void filler. In some even further embodiments, the bone void filler is loaded into its casing upon manufacture while at least one element of a reinforcement component is to be loaded into a closable casing in situ. In accordance with what is disclosed above, said fillable casing may be empty upon manufacture and to be filled with a curable matrix substance, optionally with a reinforcement phase, in situ; or it may be pre-filled with pre-impregnated or non-pre-impregnated (i.e. dry) reinforcement phase upon manufacture, and to be filled in situ with a curable matrix substance, optionally with a further (similar or different) reinforcement phase. Said fillable casing forms the backbone of the implant, and it may or may not contain one or more through holes (12) for mechanical fixing. As set forth above, the fillable casing may be closable and/or it may comprise a projecting part (14) to allow air escape upon filling of the fillable casing. The projecting part (14) may be removable.

Figure 9:
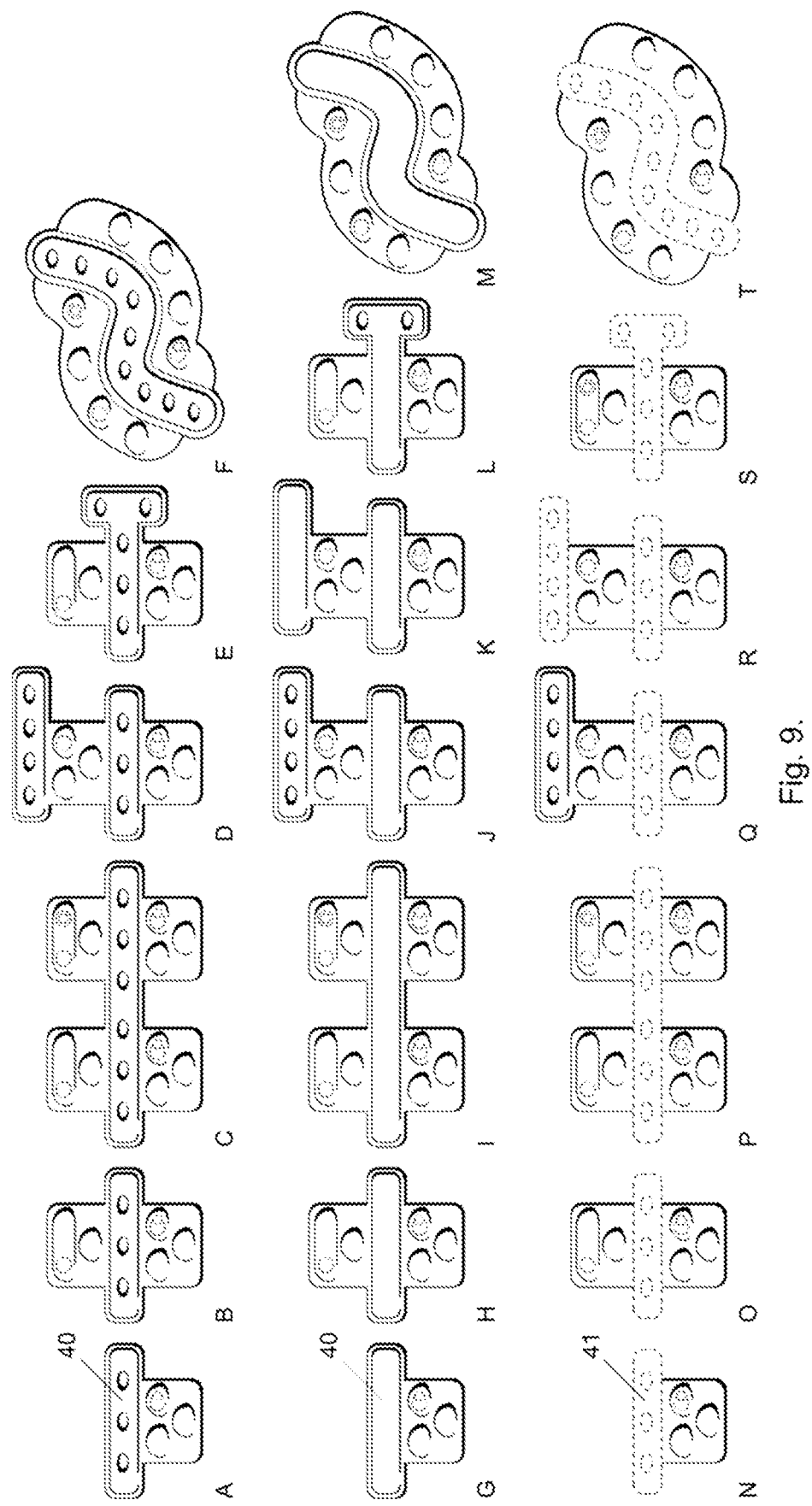
Figure 10:
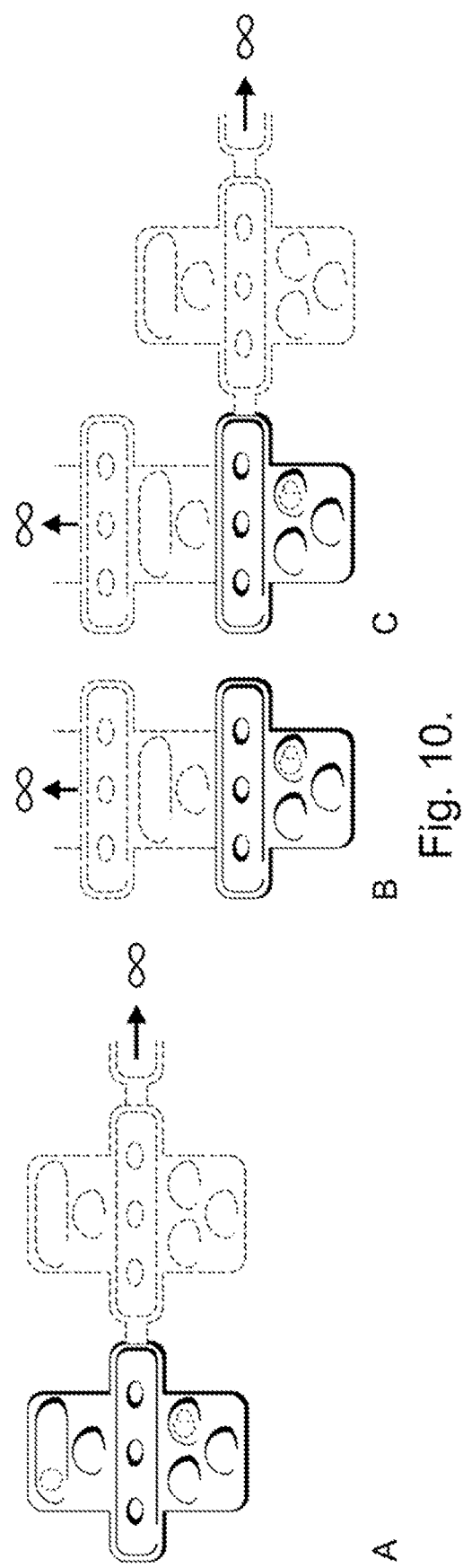
FIGS. 10A to 10C illustrate different configurations of a bone implant comprising or consisting of repeating units, each unit being a similar or dissimilar arrayed structure of casings.
Figure 11:
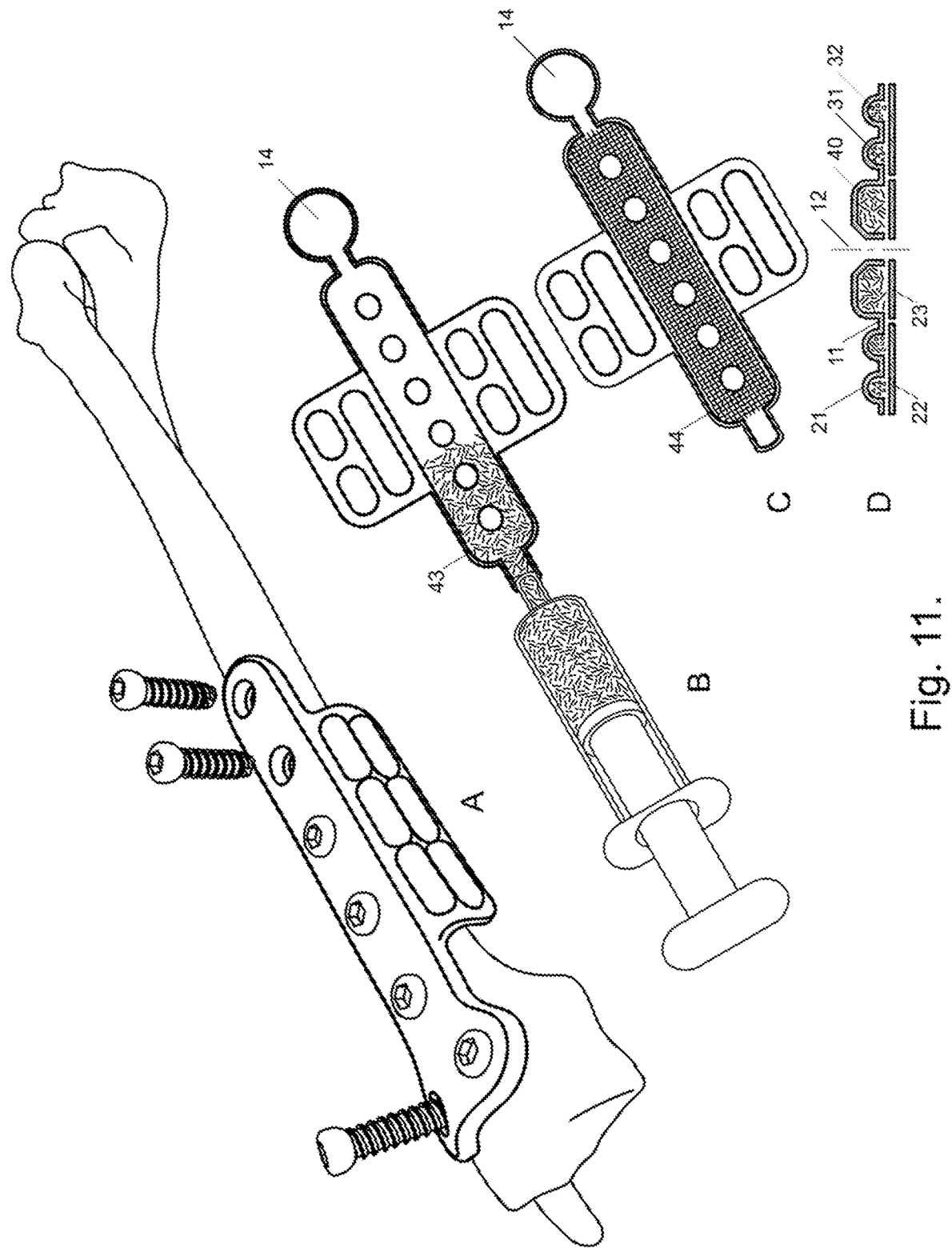
FIG. 11 C illustrates an embodiment, wherein a casing with holes may contains prepreg (44), which upon solidification serves as a reinforcement element and as the load-bearing backbone of the implant. The casing may comprise a projecting empty part (14) to allow air escape after the introduction of curable matrix monomers.

In one possible arrangement of the above embodiment, casings other that the backbone casing may be configured as one or more wing-like structures of arrayed casings (as illustrated e.g. in FIGS. 9A to 9C), at least one (i.e. some) or all of which are filled with bone void filler as disclosed above. The wing-like structures may further comprise any other casings in accordance with what is disclosed above. If the implant comprises multiple wing-like structures, they can be arranged on the same side or different, such as opposing, sides of the backbone casing. Said wing-like structures may be cut to a suitable size or shape as describes above, preferably along a sealing area (11) that connects different casings of the wing-like structure.

In accordance with the above, the present implant may contain a fillable casing with or without holes (12) extending from the top surface to the bottom surface and not being in contact with to the interior of the casing. This fillable casing can be empty or it may contain a reinforcement component. During the implantation, this fillable casing is fixed to the bone, e.g. by means of screws inserted into the holes (12) in one of the casings. Thereafter, the fillable casing is filled by a curable matrix substance in situ. Subsequently, the curable matrix substance solidifies to create a load-bearing backbone of the implant. The reinforcement component may comprise a pre-impregnated or non-pre-impregnated reinforcement phase, which phase upon the introduction and solidification of the curable matrix substance, provides the load-bearing backbone of the implant.

Each and every above-described array-like arrangement may be modified by placing the reinforcement component in its casing upon manufacture. In such cases no further filling on the clinical premises or in situ is required. If the reinforcement component is a planar structure, e.g. a plate, the holes (12) go also through the reinforcement component.

Alternatively or in addition, each and every above-described array-like arrangement may be modified by providing the reinforcement component as a structure not contained in any bioresorbable or biostable casing. Such an extraneous reinforcement phase is in contact with an array of a plurality of casings. The extraneous reinforcement component may comprise one or more through holes (12) for mechanical fixing, and/or it may secured in its place by chemical means well known in the art.

Irrespective of whether in a nested configuration, array-like configuration, or nested array-like configuration, the present implants may be constructed to have a stackable structure. In other words, the implant may have a shape configured to interconnect with other implants. Said stackable structure may be achieved, for instance, by using a mating profile, wherein one or more protrusions in one implant fit in and interlock with corresponding recesses in another implant. Thus, the mating profiles of different single implants may be in a male-female relationship. Interlocking is a convenient way of combing two or more implants according to the present invention for repairing larger bone defects.

Figure 5:
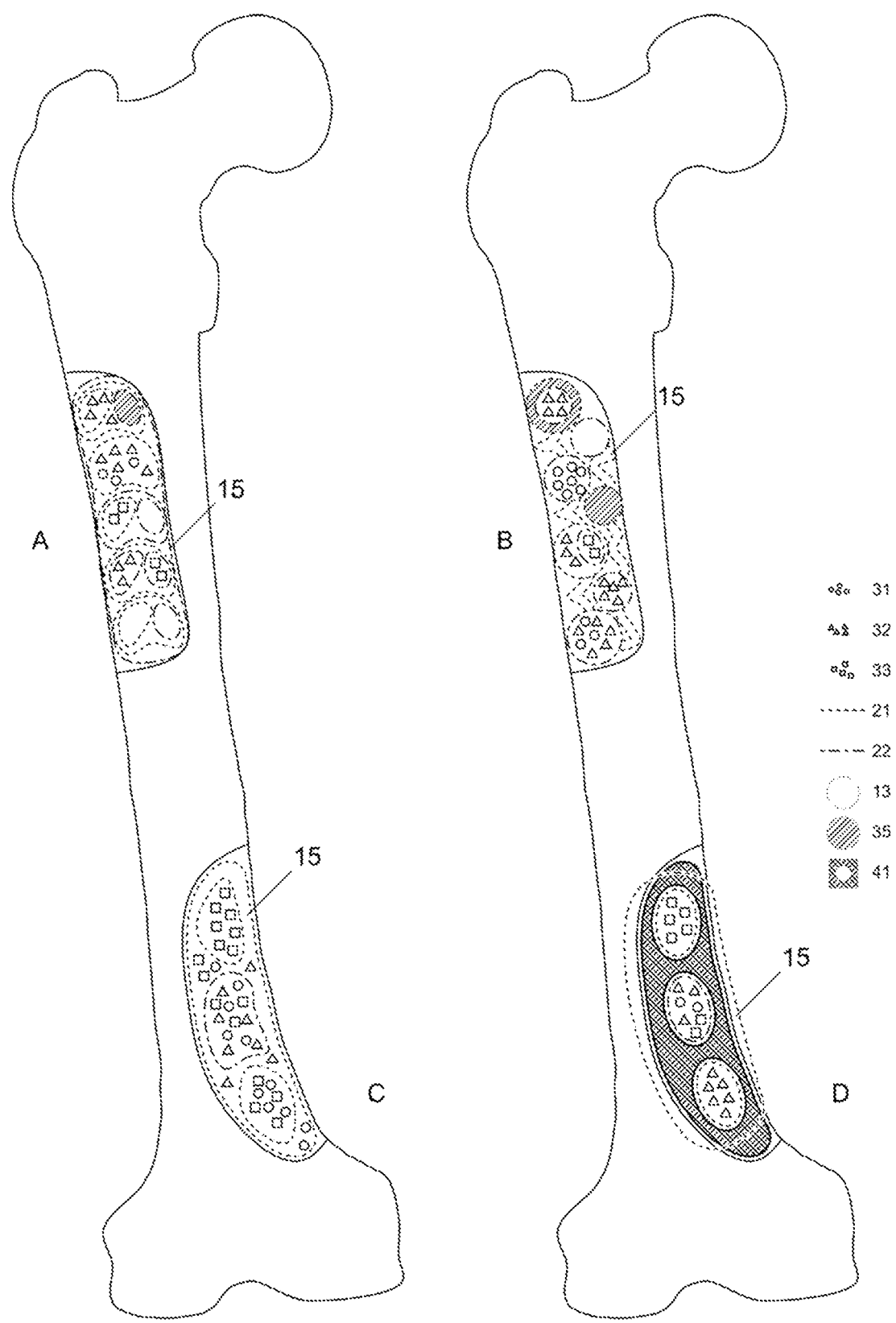
FIGS. 5A to 5D demonstrate the use of implants according to some embodiments of the present invention for the treatment of bone defects. The present implants may be implemented in conjunction with other skeletal implants, e.g. plates known in the art.

FIGS. 1D, 3D, 5A illustrate non-limiting examples of stackable implants according to the present invention.

In some embodiments, any of present implants, or a plurality of such implants, may be embedded or incorporated in an implant bulk and, thus, be referred to as "an embedded implant". As used herein, the term "implant bulk" refers any known or future implant body, core, base, mass, or the like made of any biocompatible material such as metals, polymers or ceramics. Non-limiting examples of such embedded implants are illustrated in FIGS. 4, 5D, 6B, and 7. A preferred implant bulk is an osteotomy wedge as exemplified in FIG. 7.

Figure 7:
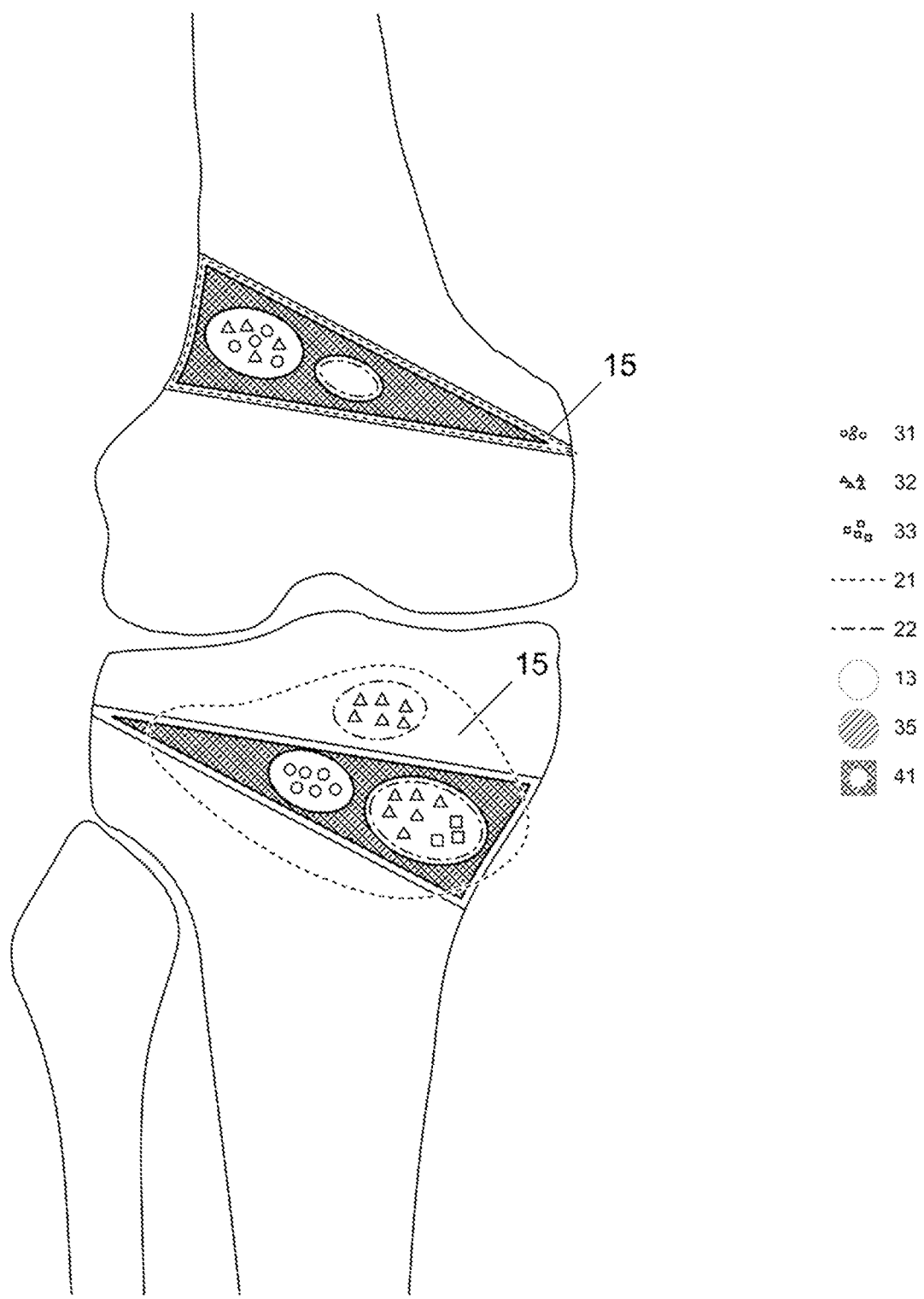
FIG. 7 illustrates the use of the present casings in osteotomy wedges by incorporation of a resilient array of casings (15) within a bulk implant (41).
Figure 8:
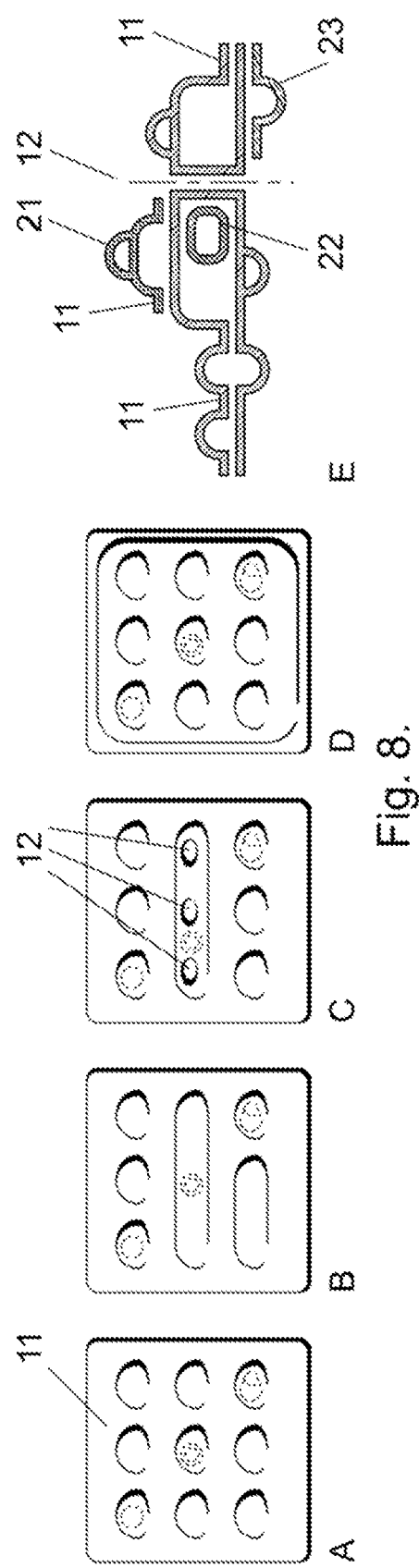
FIGS. 8A to 8E illustrate different configurations of a bone implant comprising an array of a plurality of adjacent interconnected resilient (e.g. bioresorbable) casings. The casings are interconnected through a sealing area (11) composed of the one or more resilient polymers of the casings.

FIG. 7 illustrates two examples of the present implants particularly adapted for the use as osteotomy wedges, but any of the present implants, such as those exemplified in FIGS. 1 and 2, may be employed as embedded implants for the use as osteotomy wedges. In some preferred embodiments, the present invention provides an embedded implant for use in tibial tuberosity advancement (TTA) surgery, an orthopedic procedure for repairing deficient cranial cruciate ligaments in animals, such as dogs.

Further non-limiting use examples of the present implants in veterinary orthopaedics include treatment of radial and ulnar fractures of small animals such as dogs, especially toy-breed dogs, and fractures of the third metacarpal (MC3) and third metatarsal (MT3) bones of equine, such as Thoroughbred racehorses.

The present implants and components thereof may be prepared by any method available in the art suitable for manufacturing clinical grade implants. Such methods include, but are not limited to, present and future 3D printing techniques, such as selective laser sintering (SLS) and fused deposition modelling (FDM). Alternatively or in addition, any appropriate glass-making technology, such as blowing, may be employed for manufacturing casings made of BAG. In some preferred embodiments, the implant may be prepared by vacuum pressing.

In some aspects, the present invention provides a bone grafting method wherein a bone repair site in a subject in need of bone grafting is implanted with an implant according to the present invention. Any embodiments disclosed above with respect to the implant apply correspondingly to the bone grafting method as is apparent to a skilled person.

In some aspects, the present invention provides a method for bone fracture management.

Accordingly, the present invention also relates to a method of treating a subject in need of bone grafting, bone fracture management, or local radiotherapy of benign and malignant bone tumors, by introducing an implant according to the present invention to a bone area to be treated.

In some embodiments, the implant may be secured to its place chemically, for instance by using a glue or any other bioadhesive agent, and/or mechanically as set forth above.

It will be obvious to a person skilled in the art that, as technology advances, the inventive concept can be implemented in various ways. The invention and its embodiments are not limited to the examples described above but may vary within the scope of the claims.

LIST OF REFERENCE SIGNS

10 Casing (component)
11 Sealing area
12 Holes
13 Fillable casing
14 Projecting part for air escape
15 Array of casings
20 Material of the casing
21 Polymer 1 (or composite)
22 Polymer 2 (or composite)
23 Polymer 3 (or composite)
24 BAG shell prepared by e.g. blowing or 3D-printing
30 Filler (component)
31 Filler1 (e.g. bioactive ceramic particulate)
32 Filler2 (e.g. bioactive ceramic particulate)
33 Filler3 (e.g. bioactive ceramic particulate)
34 BAG
35 Buffering solution
40 Reinforcing component
41 Implant bulk or other know reinforcement component
42 Injectable matrix without reinforcement
43 Injectable matrix with reinforcement (e.g. short fibers)
44 Prepreg
45 Ready composite

The invention claimed is:

1. A bone implant comprising an array of a plurality of adjacent polymeric casings at least one of which encases a bone void filler,
wherein said bone void filler is not attached to its casing, and at least one reinforcement component which is encased by one of said plurality of adjacent polymeric casings, which casing is other than the at least one casing that encases the bone void filler, and
wherein the at least one reinforcement component is different from the bone void filler and comprises a reinforcement phase provided as pre-impregnated with a curable matrix substance,
with the proviso that a material of the plurality of adjacent polymeric casings does not contain a curing initiator, and
wherein at least one of the casings comprises at least one through hole, wherein the at least one through hole is not open to an interior of the at least one casing comprising the at least one through hole.

2. The bone implant according to claim 1, wherein the casing of the at least one reinforcement component is filled with the reinforcement component on clinical premises or in situ.

3. The bone implant according to claim 1, wherein the at least one reinforcement component comprises a further reinforcement phase and a further curable matrix substance.

4. The bone implant according to claim 1, wherein the reinforcement phase comprises material selected from carbon, glass, ceramic, metal, polyethylene, polyamide, polyimide, acrylate polymer, and any mixtures or combinations thereof.

5. The bone implant according to claim 4, wherein the reinforcement phase is in the form selected from the group consisting of randomly oriented fibres, intermingled fibres, overlaid fibres, juxtaposed fibres, woven or non-woven structures, fabrics or mats, particulates, whiskers, and 3D-printed fiber structures.

6. The bone implant according to claim 1, wherein the curable matrix substance is selected from the group consisting of substituted, unsubstituted, or functionalized polyesters, polyethers, polyurethanes, polyethylene, epoxy resins, acrylate polymers and natural rubber.

7. The bone implant according to claim 6, wherein the acrylate is selected from the group consisting of dimethacrylates, methacrylates, methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA), and any mixtures or combinations thereof.

8. The bone implant according to claim 1, wherein the casing of the at least one reinforcement component comprises a removable projecting part.

9. The bone implant according to claim 1, wherein the at least one reinforcement component comprises material selected from the group consisting of metals, reinforced or non-reinforced composites, self-reinforced polymers, ready composites, and bioresorbable materials.

10. The bone implant according to claim 1, wherein the at least one reinforcement component is in the form of a plate.

11. The bone implant according claim 1, wherein said at least one through hole is comprised in the casing of the at least one reinforcement component.

12. The bone implant according to claim 1, wherein the at least one reinforcement component comprises at least one through hole.

13. The bone implant according to claim 1, wherein the at least one reinforcement component forms a backbone of the bone implant.

14. The bone implant according to claim 13, wherein the casings other than that of the at least one reinforcement component are arranged in one or more arrayed wing-like structures located on the same or different sides of the backbone.

15. The bone implant according to claim 1, wherein at least one of the casings encases a series of any number of adjacent and/or nested inner casings.

16. The bone implant according to claim 1, wherein adjacent polymeric casings in the plurality of adjacent polymeric casings are made of a material selected from the group consisting of bioresorbable polymers, biostable polymers, composites of bioresorbable polymers, composites of biostable polymers, composites of bioresorbable polymers and bioactive glasses, and composites of bioresorbable polymers, and calcium phosphate-based ceramics.

17. The bone implant according to claim 1, wherein said bone void filler is selected from the group consisting of calcium phosphate-based ceramics, bioactive glasses, bioactive glass-ceramics, composites of bioactive glasses or glass-ceramics and bioresorbable polymers, allograft or autograft bone, or fully or partly demineralized bone matrix.

18. The bone implant according to claim 17, wherein, the bone void filler comprises bioactive ceramics and a radioactive isotope.

19. The bone implant according to claim 18, wherein the radioactive isotope is Holmium.

20. The bone implant according to claim 1, wherein at least one of the casings encases a substance selected from the group consisting of buffering solutions, antibiotics, immunosuppressants, immunostimulators, anti-inflammatory agents, proteins, growth factors, cells, air, inert gasses, or any mixtures or combinations thereof.

21. The bone implant according to claim 1, having a stackable profile.

22. The bone implant according to claim 1, wherein at least one of the casings and/or contents of at least one of the casings are prepared by 3D printing or vacuum pressing.

23. A set of two or more bone implants according to claim 1.

24. The set according to claim 23, wherein the bone implants have matching mating profiles.

25. A method of treating a human or animal subject in need of bone grafting, bone fracture management, or local radiotherapy of benign and malignant bone tumors, said method comprising:
    introducing the bone implant according to claim 1 to a bone area to be treated.

* * * * *